United States Patent [19]
Horn et al.

[11] Patent Number: 5,574,368
[45] Date of Patent: Nov. 12, 1996

[54] APPARATUS AND METHOD FOR INDUCING EDDY CURRENTS IN A STRUCTURE FOR MAGNETO-OPTIC TESTING

[75] Inventors: Michel Horn, South Setauket; Stanley M. Reich, Jericho, both of N.Y.

[73] Assignee: Northrop Grumman Corporation, Los Angeles, Calif.

[21] Appl. No.: 524,845

[22] Filed: Sep. 7, 1995

[51] Int. Cl.⁶ ............................. G01N 27/82; G01R 33/12
[52] U.S. Cl. .......................... 324/228; 324/235; 324/238
[58] Field of Search .................................. 324/232, 235, 324/228, 238, 262

[56] References Cited

U.S. PATENT DOCUMENTS 4,379,261  4/1983  Lakin ........................................ 324/232
4,625,167  11/1986 Fitzpatrick ............................... 324/235

*Primary Examiner*—Walter E. Snow
*Attorney, Agent, or Firm*—Terry J. Anderson; Karl J. Hoch, Jr.

[57] ABSTRACT

In order to control the direction of a magnetic field induced by a current sheet in a sheet conductor, relative to anomalies in a test sample, the current sheet is either rotated relative to the sheet conductor, by using either electrical or mechanical commutation of the current sheet, or the phases of plural independent current sheets in the sheet conductor are shifted relative to each other.

19 Claims, 8 Drawing Sheets

APPARATUS AND METHOD FOR INDUCING EDDY CURRENTS IN A STRUCTURE FOR MAGNETO-OPTIC TESTING

BACKGROUND OF THE INVENTION

1. Field of the Invention

This invention relates to the area of non-destructive inspection technology known as magneto-optic/eddy current imaging.

2. Discussion of Related Art

Conventional magneto-optic/eddy current imaging technology has been used to generate real-time images of defects, such as fatigue, cracks and corrosion, in metals, and cracks, delamination and other defects in non-metallic structures. Instruments which utilize the Faraday magneto-optic effect, first discovered in 1845, operate by employing a material which rotates the plane of polarization of polarized light passing through the material as a function of an applied or developed normal magnetic field.

As shown in FIG. 1, a typical magneto-optic effect sensor employs a magneto-optic crystal, such as a garnet-iron crystal 1, coated with a dielectric reflective layer 2 which causes light passing through the crystal from a source 3 and polarizer 4 to reflect back through the crystal to a polarization detector 5, as shown in FIG. 1. On each pass of polarized light through the crystal, the initial polarization is rotated in a direction determined by an the applied magnetic field B. Although the reflective coating 2 is not essential, by utilizing a double pass configuration, the rotational sensitivity of the sensor is increased by a factor of two.

Such a sensor can be used for non-destructive structural inspections by applying an alternating magnetic field to the structure being tested or inspected test. The alternating magnetic field induces a uniform flow of eddy currents in the structure. Pursuant to Lenz's law, the eddy currents in turn create weak secondary magnetic fields which oppose the applied field and are therefore normal to the eddy currents and to the plane of the sensor. The low intensity secondary magnetic fields cause a local rotation of the plane of polarization of the light passing through the sensor. The local rotation of the plane of polarization creates a spatial image on the sensor, which is latent until light passing through the sensor is intercepted by the polarization detector or analyzer 4 which converts variations in polarization to intensity modulation. Any cracks, surfaces, or sub-surface anomalies in the test sample or structure being inspected will disrupt the flow of eddy currents and therefore vary the secondary magnetic fields, the variations being detected by the magneto-optic sensor in order to determine the nature and extent of the anomaly.

A disadvantage of conventional systems using the type of sensor shown in FIG. 1 is that when an induced eddy current is parallel to a crack or other anomaly, the level of disturbance available to create the perpendicular secondary magnetic field needed to rotate the local polarization in the magneto-optic crystal, and thereby detect the crack, will be negligible, increasing susceptibility of the image formed by the sensor to background interference effects. As a result, conventional magneto-optic measuring instruments must be manually rotated in order to ensure that anomalies in all directions are detected. This slows the inspection process, puts a limitation on miniaturization and the use of automized pattern detection techniques, and makes remote un-manned inspections using magneto-optic technology impossible.

SUMMARY OF THE INVENTION

It is a first objective of the invention to provide a magneto-optic effect inspection apparatus which permits optimization of normal magnetic fields induced in a magneto-optic crystal without the need to manually rotate the equipment in order to compensate for the orientation of anomalies in the structure being inspected.

It is a second objective of the invention to provide a magneto-optic effect sensor capable of remote unmanned inspections, in normal magnetic fields caused by crack/corrosion induced disruption of eddy currents in a structure being inspected are optimized, thus reducing background interference effects in the sensor image as seen by the viewer.

It is a third objective of the invention to provide an enhanced magneto-optically generated image which makes it possible for an operator to detect cracks and other defects not visible in conventional magneto-optic sensor images, and to perform the detection more rapidly than is possible with prior magneto-optic sensors.

It is a fourth objective of the invention to increase the signal-to-noise or image-to-background ratio of a magneto-optically generated image sufficiently to enable automatic detection methods using pattern recognition techniques to be employed, thus making possible completely unmanned monitoring of cracks and corrosion, and the use of miniaturized remotely operated eddy current detector robots.

These objectives are achieved by providing an apparatus and method which enables the direction of eddy currents induced in a test sample to be rotated without physically rotating the associated measuring instrument. The eddy currents are instead rotated by rotating the applied magnetic field which induces the eddy currents in the structure. The applied magnetic field is generated using a sheet conductor in which a single current sheet is caused to flow. This allows the applied field, and therefore the induced eddy currents, to be rotated by simply changing the direction of the sheet current using a commutator which is either mechanically rotated or electronically rotated, or by controlling the relative phase difference between plural AC current sheets flowing in the sheet conductor.

DETAILED DESCRIPTION OF THE PREFERRED EMBODIMENTS

Figure 1:
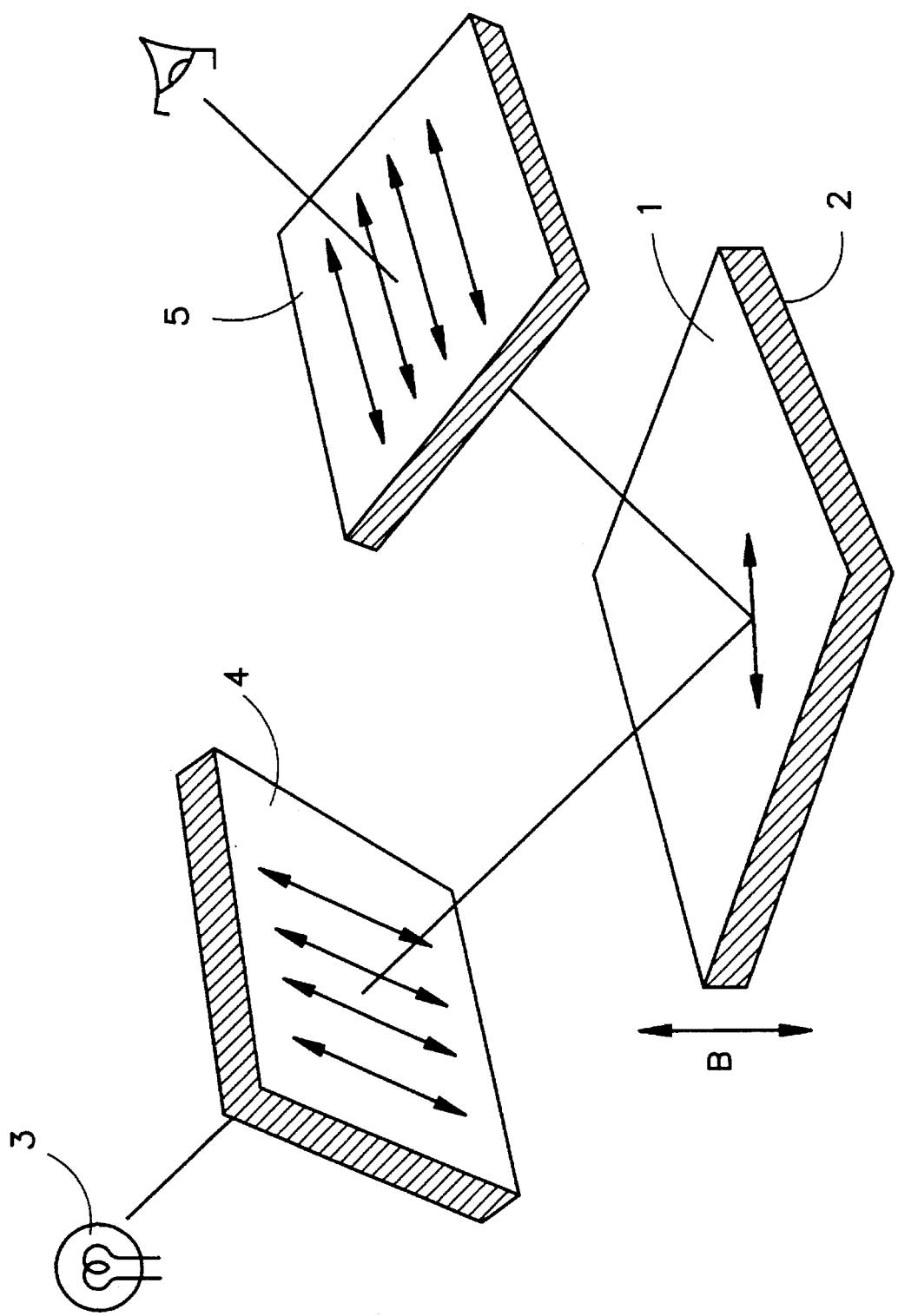
FIG. 1 is a schematic diagram of a conventional Faraday magneto-optic effect reflective crystal sensor.
Figure 2:
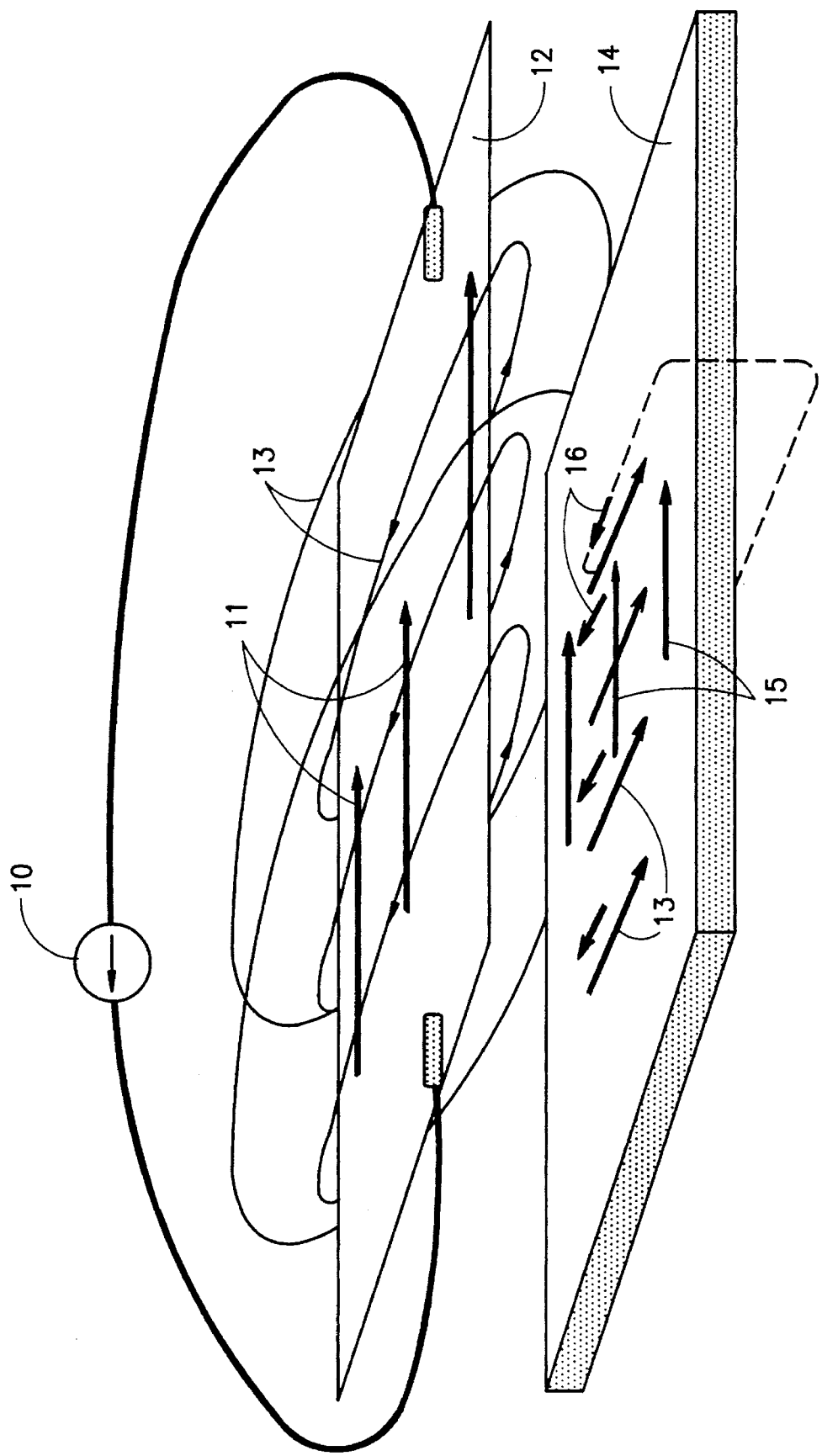
FIG. 2 is a schematic diagram showing the principles which control the arrangement for generating an applied magnetic field used by the apparatus and method of a preferred embodiment of the invention, including illustration of the eddy currents and secondary fields resulting from application of the magnetic field to an ideal test sample with no cracks or anomalies or any kind.
Figure 3:
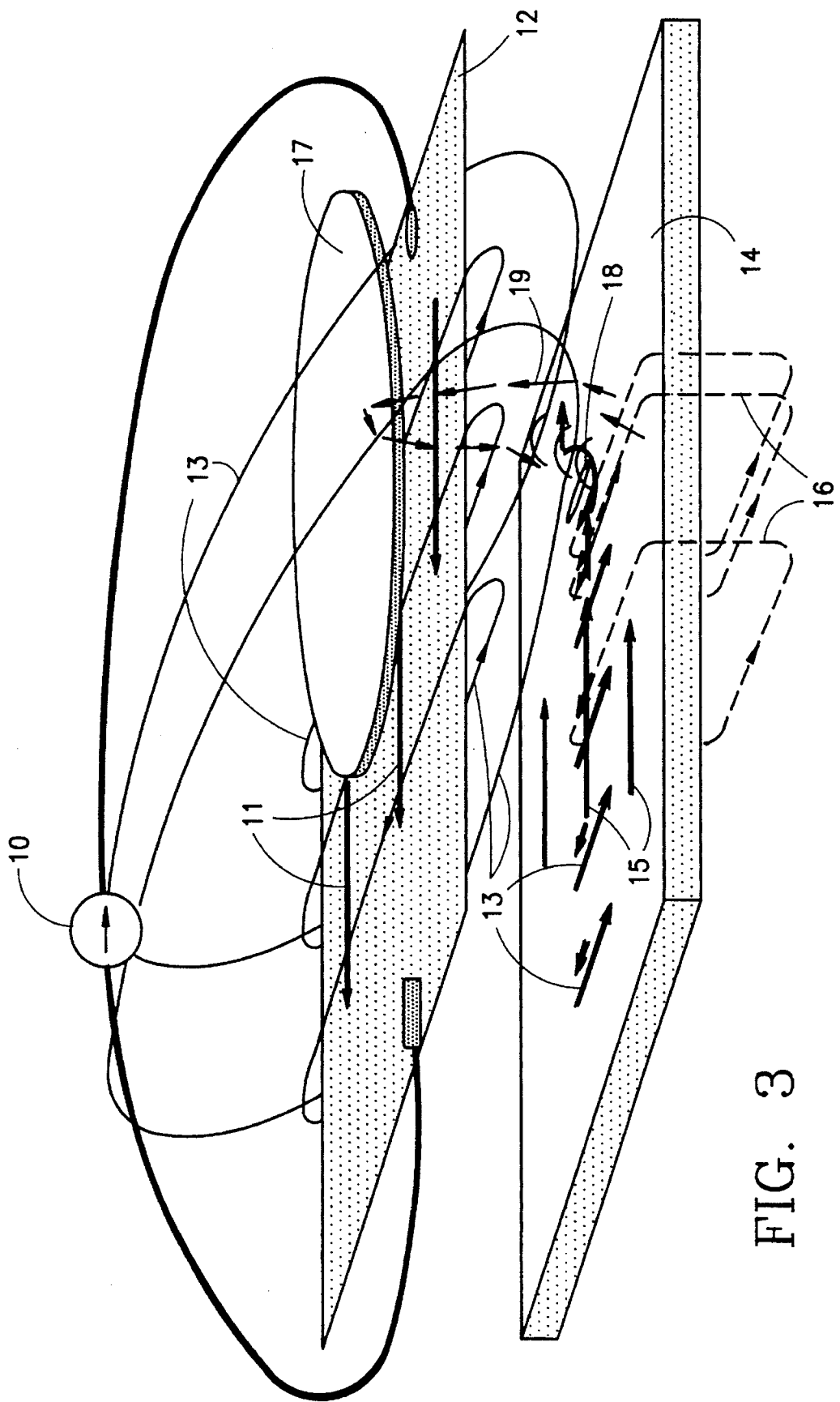
FIG. 3 and 3A are schematic diagrams illustrating the manner in which a crack affects the eddy currents and secondary magnetic fields induced by the magnetic field generating arrangement of FIG. 2.

FIGS. 2–3 illustrate the manner in which eddy currents are induced in a non-ferrous test sample or structure by an applied magnetic field. The induced eddy currents behave according to the rule derived from Faraday's law which, in its integral form, states that a voltage drop (emf) must exist about any path that surrounds a time varying change in magnetic flux, as follows:

$$emf = -\int_s \frac{\partial B}{\partial t} \cdot n \, da$$

where S is the surface bounded by the closed path around which the emf is induced. If the path in question lies inside the conductor in which the flux is changing, the voltage will induce a current flow or eddy current.

Eddy currents tend to flow around the surface of a conductor in the manner of a sheet current solenoid, and in a direction opposite to the inducing flux change. As a result, the H-field of the eddy current is opposite to the applied field. This is the field that intercepts the cracks and other anomalies in the sample.

The relationship between the applied field, induced eddy currents, and resulting secondary fields for a structure with no anomalies is illustrated in FIG. 2. In the illustrated arrangement, a alternating current source 10 causes an alternating sheet current 11 to flow in sheet conductor 12, which in turn generates an alternating primary magnetic field 13 which follows the right hand rule and is at right angles to the current flow. This field passes through the test sample 14 and, in accordance with Faraday's law, induces a voltage drop across the sample 14. The voltage drop causes an eddy current 15 to flow. The eddy current 15 in turn generates a secondary magnetic field 16 which, according to Lenz's law, opposes the applied field 13.

Figure 3A:
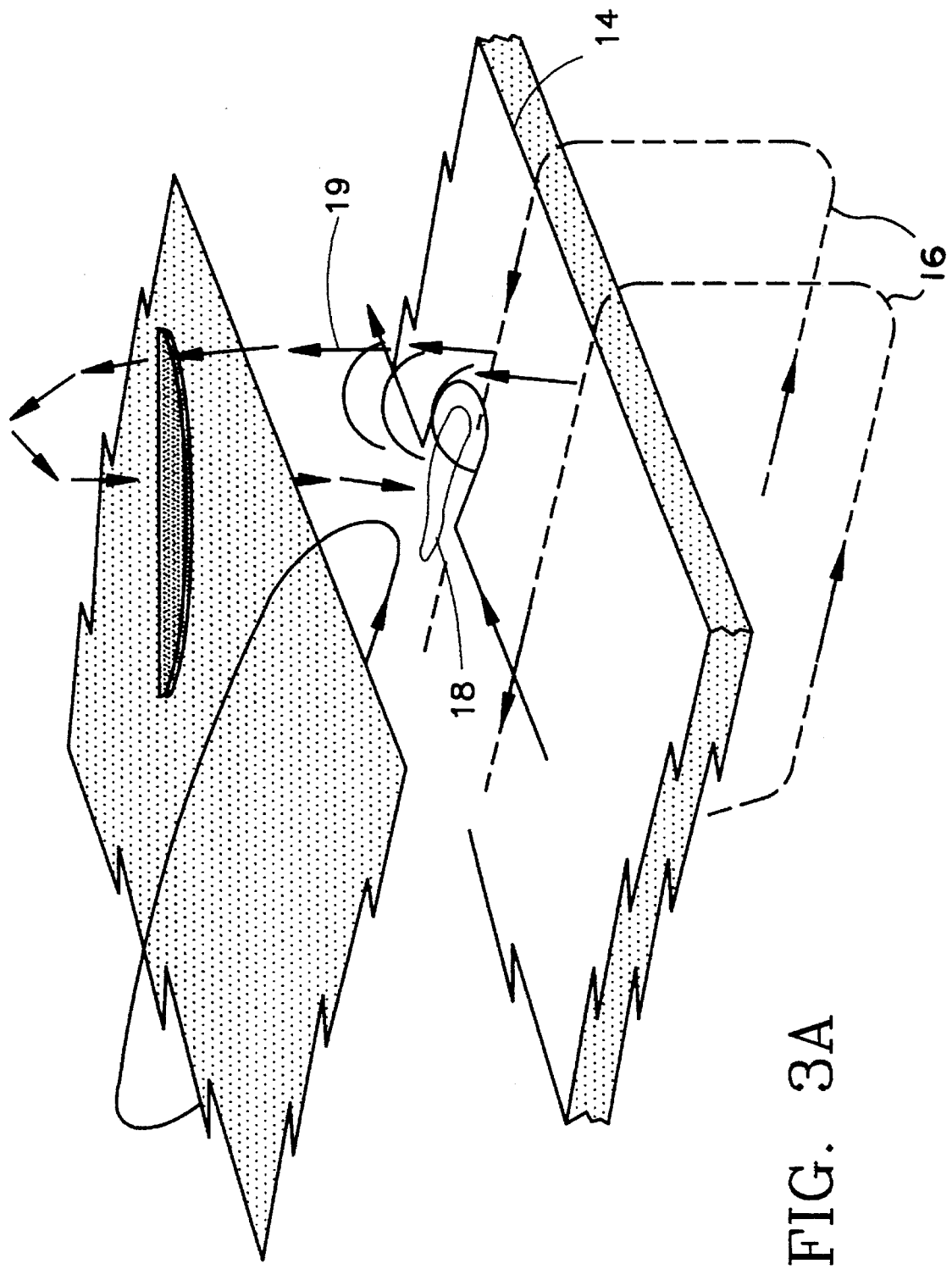

As long as the sample is uniform, the secondary magnetic fields 16 caused by the eddy current flow takes the form of one large solenoidal magnetic field, as shown in FIG. 2, that couples uniformly into, but not necessarily normal to, the magneto-optic sensor 17 (shown in FIG. 3, but not in FIG. 2). If a crack 18 or other anomaly disrupts the uniform flow of the alternating eddy current, on the other hand, causing it to change its local path in the test sample by flowing around the crack, as shown in FIGS. 3 and 3A, the opposing magnetic field also is disrupted. As the eddy current flows around the crack, a local opposing magnetic field 19 is generated. This opposing magnetic field changes polarity on either side of the crack as the AC eddy current alternates polarity and thus can, in principle, be detected by the sensor. However, in practice, if the crack 18 is very fine and parallel to the flow of the eddy current in the test sample, since there is no impedance to speak of to the current flow, no local disruption of the current occurs. In that case, in order to see that particular crack, using conventional apparatus, the operator must rotate the entire test instrument in order to obtain an eddy current which is normal to the crack. The apparatus and methods of the preferred embodiments avoid this problem by rotating the applied magnetic field relative to the structure being tested or inspected without rotating either the sheet conductor or the sensor.

Figure 4:
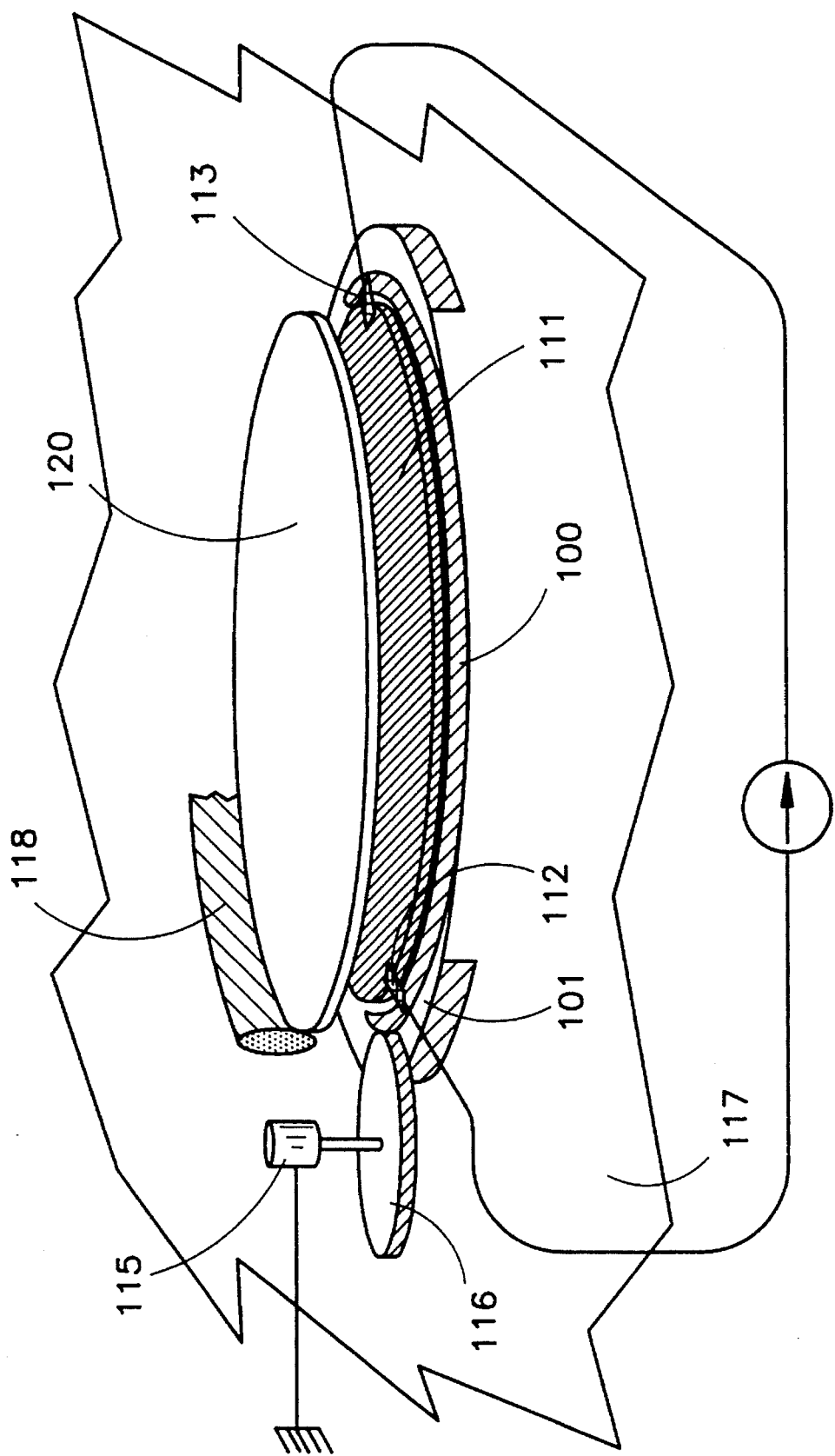
FIG. 4 is a perspective view of a mechanical commutator for rotating a current sheet in a magneto-optic test apparatus in order to rotate an applied magnetic field according to a first preferred embodiment of the invention.

In the first two preferred embodiments illustrated herein, the eddy currents are rotated by changing the direction of sheet currents which generate the applied magnetic field. In the embodiment shown in FIG. 4, a mechanized ring-shaped commutator 100 supported on a bearing structure 101 is arranged to rotate around the perimeter of a thin sheet conductor 111. The commutator 100 carries at least two diametrically opposed electrodes 112 and 113 which are in sliding contact with the conductor 111 so that the electrodes cause a sheet current to flow in the conductor when connected to current source 114. The location at the diametrically opposed pair of electrodes 112 and 113 contact the conductor 111 determines the direction of the current flow, and the current flow is thus varied as the commutator and electrodes are rotated around the current sheet. The commutator is preferably rotated directly or remotely by a stepper or other electric motor 115 through, for example a gear drive 116.

The test instrument of this embodiment may also include, in addition to the above-described arrangement for applying a primary magnetic field to the test sample or inspected structure 117, by generating a current sheet in conductor 111, an arrangement 118 for applying a permanent bias field to the test sample or structure being inspected, in a manner known to those skilled in the art. Details of the motor, drive and bearing structure will of course be readily filled-in by those skilled in the art and, in addition, those skilled in the art will appreciate that a variety of sensors 120, including the conventional garnet crystal type of sensor, may effectively be employed with the preferred magnetic field rotation apparatus.

Figure 5:
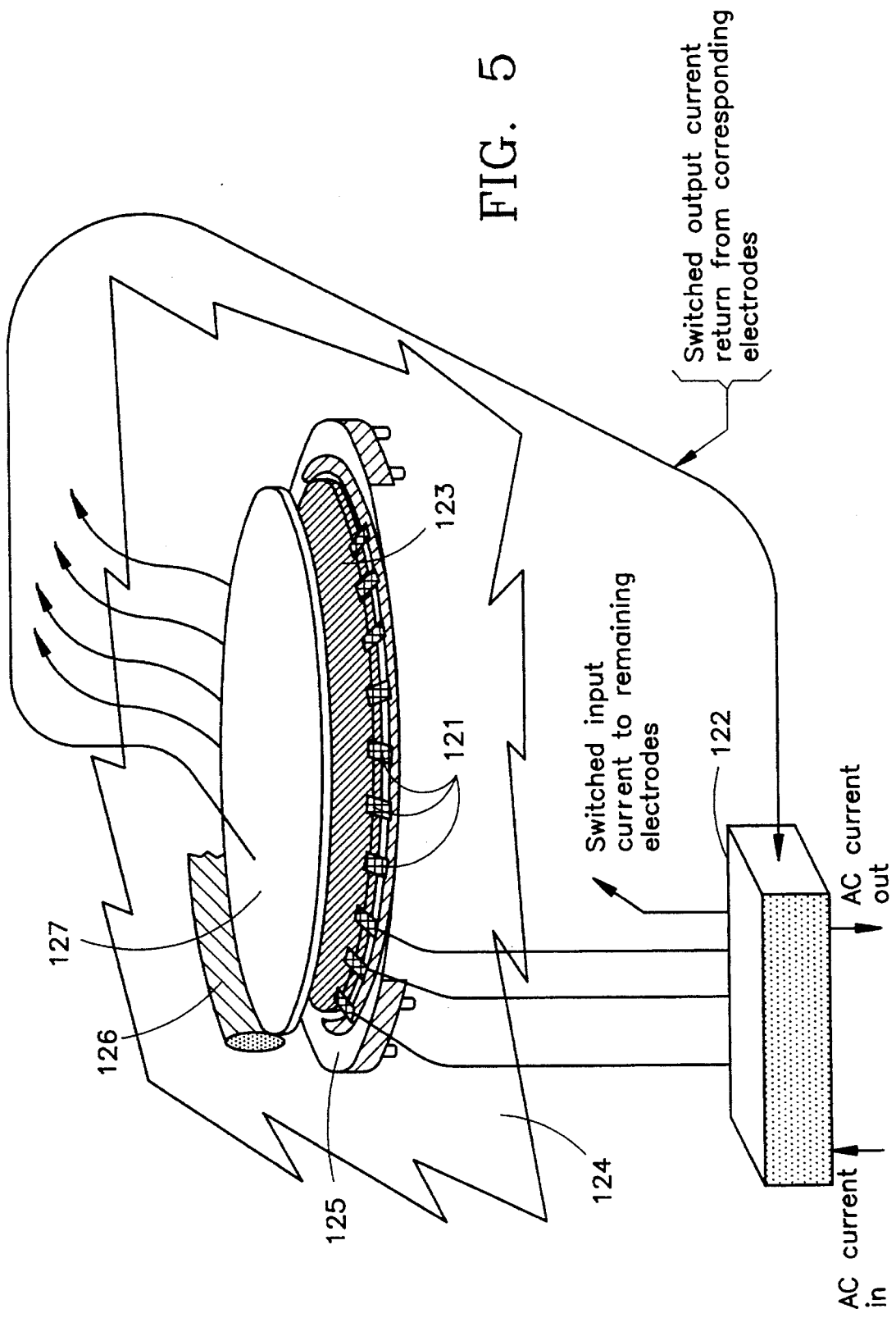
FIG. 5 is a perspective view of an electronic commutator for rotating a current sheet in a magneto-optic test apparatus in order to rotate an applied magnetic field according to a second preferred embodiment of the invention.

An alternate method of rotating the sheet current which generates the applied magnetic field is to electronically commutate the sheet current, as shown in FIG. 5. The electronic commutator includes a set of pairs of diametrically opposed electrodes 121 for each desired current direction and a switching circuit 122 to electronically switch the electrical connection among the array of permanently attached electrodes around the perimeter of the conductor 123 that carries the sheet current. As with the embodiment shown in FIG. 4, the flow of current in the sheet conductor 123 produces a normal magnetic field that passes through the structure under test 124. This field in turn produces an eddy current in the structure in a plane parallel to that of the conductor sheet and in a direction which opposes the applied magnetic field. As a result, rotating the current in the sheet conductor 123 rotates the eddy currents in the sample or structure under test 124. As in the example of a mechanical commutator, a support structure for the conductor as well as a biasing arrangement can easily be provided by those skilled in the art, and a variety of sensors 127 can be used to detect the resulting secondary magnetic fields as described above.

Figure 6:
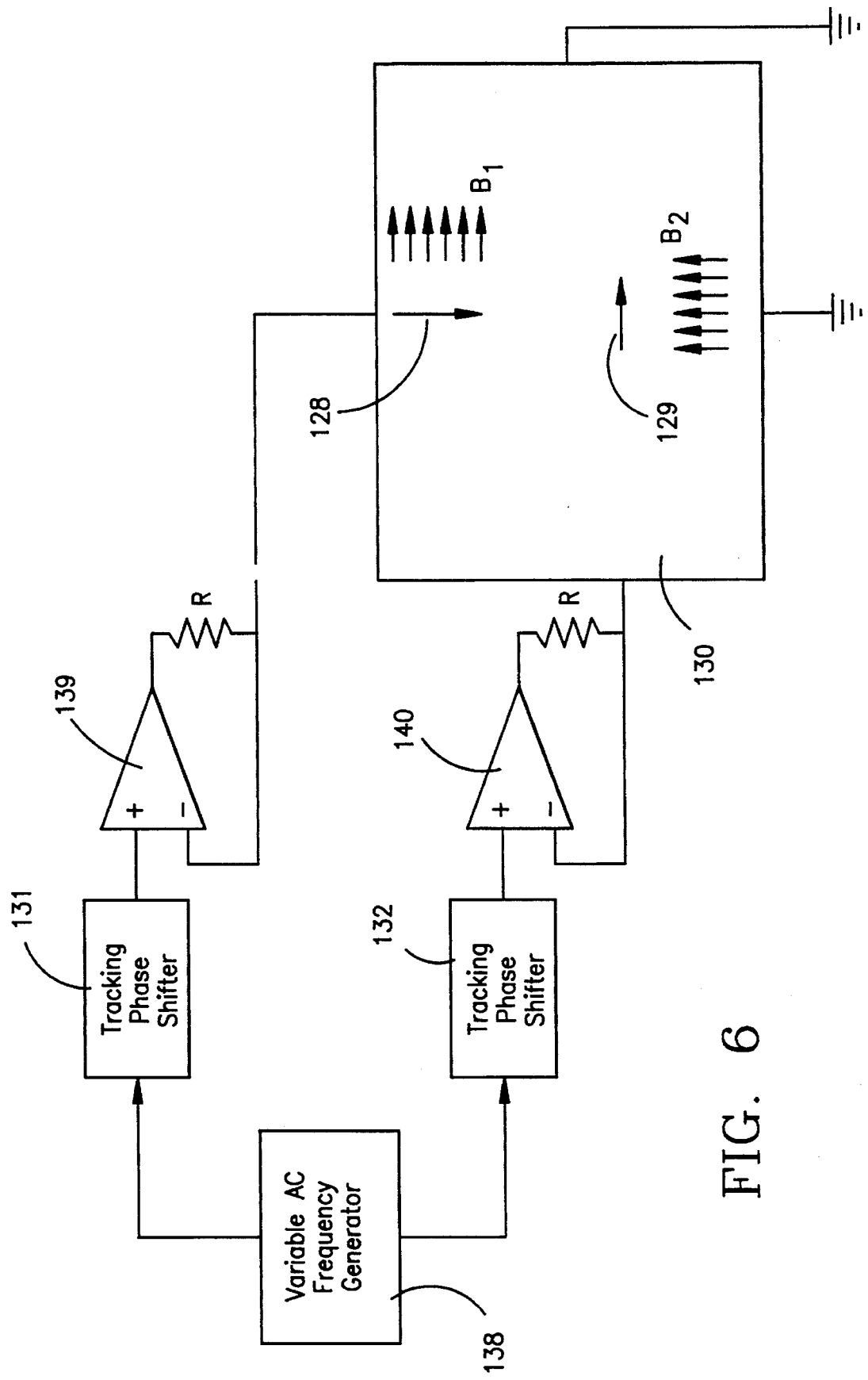
FIG. 6 is a schematic diagram of an arrangement for rotating an applied magnetic field by controlling the phases of multiple current sheets in a magneto-optic test apparatus according to a third preferred embodiment of the invention.

FIG. 6 shows an apparatus and method of eddy current rotation according to a third preferred embodiment of the invention. This embodiment involves rotating the resultant magnetic field produced by the interaction of two magnetic fields $B_1$ and $B_2$ generated by independent AC sheet currents 128 and 129 flowing in a thin sheet conductor 130 to obtain the primary applied magnetic field. Rotation of the applied magnetic field is controlled by controlling, using phase shifters 132 and 133, the relative phase difference between the AC current sheets 128 and 129 flowing in the conductor 130. As in the previous two embodiments, the applied magnetic field is caused to pass through a test sample (not shown) to produce an eddy current flow in the plane of the sample in a direction that opposes the flux change of the applied magnetic field. The resulting eddy currents flow in an angular direction in the sample plane which is a direct function of the relative phase between the sheet currents. Since the phase enhanced rotation is frequency sensitive, compensation can be provided by a variable AC generator 138 to ensure that the phase change is proportional to a controlled change independent of frequency. Associated electronic circuits such as comparators 139 and 140 can be used to generate wave shapes which will form various search and track patterns in the sample.

Figure 7:
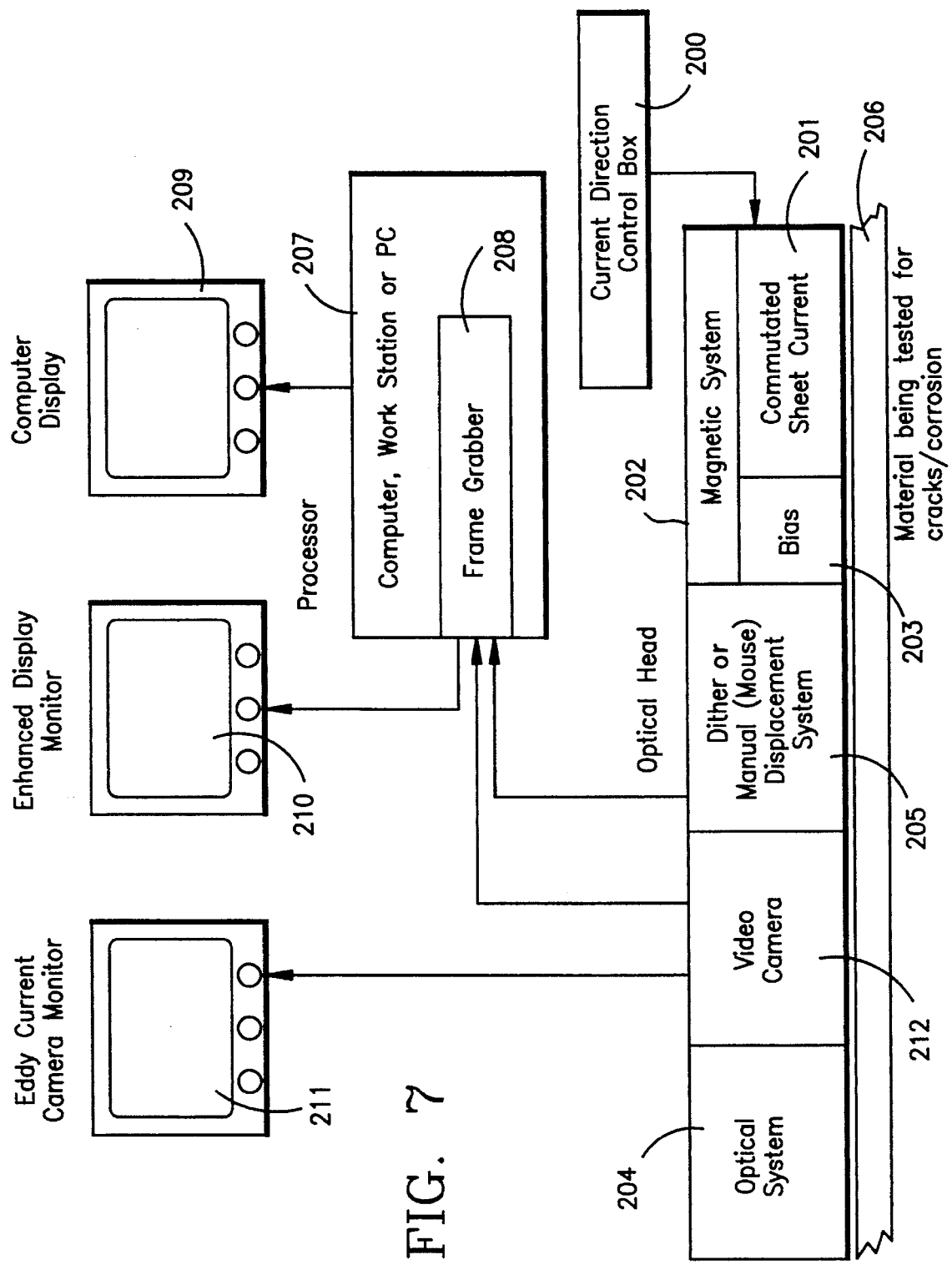
FIG. 7 is a block diagram of a magneto-optic eddy current camera with a background cancellation system and a rotatable current sheet of the type illustrated in FIGS. 4–6.

A complete test or inspection system utilizing the preferred sheet current rotating apparatus is shown in FIG. 7. The preferred current rotating apparatus includes a current direction controller 200 which can include either a mechanical or electrical commutation control, or a phase control as described above, for controlling the sheet current 201 in a sheet conductor. The magnetic system 202 may also include a bias magnet 203. The sensor (optical head), optics 204, and other elements of the overall inspection system form no part of the present invention, but it is noted that the inspection system may include a displacement system 205 and/or a dithering system as described in copending application Ser. No. 08/167,425, filed Dec. 15, 1993 (now U.S. Pat. No. 5,446,378), for background cancellation, and also a video camera 212 for allowing the operator to manually guide the sensor and conductor over the sample under test 206 using the displacement system. Because the sensor and magnetic system do not have to be rotated as they are displaced over the structure being inspected, the system can easily be adapted to perform remote unmanned inspections, for example by using robotics to displace the apparatus relative to the test sample.

Control is provided by, for example, a computer, work station, or PC 207 which includes a frame grabber 208, and a monitor 209. In the system shown in FIG. 7, images of the sample under test 206 are displayed on an enhanced display monitor 210 and the output of the magneto-optic sensor is displayed on a separate monitor 211 for visual evaluation. In addition, it is anticipated that the improved signal-to-noise or image-to-background ratio of the images will enable pattern recognition techniques to be employed, permitting completely automated operation of the system.

Having thus described several specific preferred embodiments of the invention in terms which will enable those skilled in the art to make and use the invention, it will nevertheless be appreciated that numerous variations and modifications are possible within the scope of the invention. Consequently it is intended that the invention not be limited by the above description or drawings, but rather that it be limited solely by the appended claims.

We claim:

1. Apparatus for inducing eddy currents in a structure for magneto-optic testing, comprising:

a conductor sheet;

means for causing a sheet current to flow through the conductor sheet and thereby generate an alternating primary magnetic field surrounding said sheet, the primary magnetic field in turn inducing eddy currents in the structure, the eddy currents in turn generating an opposing magnetic field;

means for sensing the opposing magnetic field: and means for rotating the primary magnetic field by varying the sheet current in the conductor sheet.

2. Apparatus as claimed in claim 1, wherein the sheet current varying means comprises means for controlling a direction of the sheet current in the conductor sheet.

3. Apparatus as claimed in claim 2, wherein the means for controlling a direction of the sheet current comprises a mechanical commutator.

4. Apparatus as claimed in claim 3, wherein the mechanical commutator includes at least two electrodes fixed to a ring which is rotatable relative to the conductor sheet, the electrodes being in slidable contact with the sheet, and means for supplying an alternating current to the electrodes and thereby to the sheet, the sheet current flowing between the electrodes so that the direction of the sheet current varies as the ring rotates relative to the conductor sheet, with the orientation of the electrodes relative to the sheet determining the direction of the sheet current.

5. Apparatus as claimed in claim 4, wherein the ring is rotated by a motor.

6. Apparatus as claimed in claim 2, wherein the means for controlling a direction of the sheet current comprises an electrical commutator.

7. Apparatus as claimed in claim 6, wherein the electrical commutator comprises a plurality of diametrically opposed pairs of electrodes fixedly positioned around the conductor sheet and means for selectively supplying current to at least one of the electrode pairs and thereby to the conductor sheet, the position of the at least one pair being supplied with current determining the direction of the sheet current in the conductor sheet.

8. Apparatus as claimed in claim 1, wherein the sheet current varying means comprises means for supplying a second sheet current independent from the first sheet current to the conductor sheet and means for shifting the relative phases of the respective sheet currents.

9. Magneto-optic test apparatus, comprising:

a conductor sheet;

means for causing a sheet current to flow through the conductor sheet and thereby generate an alternating primary magnetic field surrounding said conductor sheet, the primary magnetic field in turn inducing eddy currents in the structure, the eddy currents in turn generating an opposing magnetic field;

a magneto-optic sensor positioned relative to the test sample to sense the opposing magnetic field by changing a polarization of polarized light passing through the sensor according to a direction of the opposing magnetic field; and means for rotating the primary magnetic field by varying the sheet current.

10. Apparatus as claimed in claim 9, further comprising means for displacing the sensor and conductor sheet relative to the structure under inspection, whereby the sheet current can be rotated as the sensor and conductor sheet are guided across the structure without the need for rotating either the sensor or conductor in order to detect anomalies at any point in the structure.

11. A method of inducing eddy currents in a structure for magneto-optic testing, comprising the steps of:

causing a sheet current to flow in a conductor sheet, thereby generating an alternating primary magnetic field surrounding the conductor sheet, the primary magnetic field in turn inducing eddy currents in a structure under inspection, the eddy currents in turn generating an opposing magnetic field;

measuring the opposing magnetic field; and rotating the primary magnetic field by varying the sheet current in the conductor sheet.

12. A method as claimed in claim 11, wherein the step of varying the sheet current comprises the step of controlling a direction of the sheet current in the conductor sheet.

13. A method as claimed in claim 12, wherein the step of controlling a direction of the sheet current comprises the step of mechanically commutating the sheet current.

14. A method as claimed in claim 13, wherein the step of mechanically commutating the sheet current comprises the steps of rotating, relative to the conductor sheet, a ring to which at least two electrodes are fixed, the electrodes being in slidable contact with the sheet, and supplying an alternating current to the electrodes and thereby to the sheet, the sheet current flowing between the electrodes so that the direction of the sheet current varies as the ring rotates relative to the conductor sheet, with the orientation of the electrodes relative to the sheet determining the direction of the sheet current.

15. A method as claimed in claim 12, wherein the step of controlling a direction of the sheet current comprises the step of electrically commutating the sheet current.

16. A method as claimed in claim 15, wherein the step of electrically commutating the sheet current comprises the step of selective applying alternating current to at least one of a plurality of diametrically opposed pairs of electrodes fixedly positioned around the conductor sheet, the position of the at least one pair being supplied with current determining the direction of the sheet current in the conductor sheet.

17. A method as claimed in claim 11, wherein the step of controlling the sheet current comprises the steps of supplying a second sheet current independent from the first sheet current to the conductor sheet and shifting the relative phases of the respective sheet currents.

18. A method of magneto-optic testing, comprising the steps of:

causing a sheet current to flow in a conductor sheet, thereby generating an alternating primary magnetic field surrounding the conductor sheet, the primary magnetic field in turn inducing an eddy current in a structure under inspection, the eddy currents in turn generating an opposing magnetic field;

positioning a magneto-optic sensor relative to the structure under inspection to sense the opposing magnetic field by changing a polarization of polarized light passing through the sensor according to the direction of the opposing magnetic field; and rotating the primary magnetic field by varying the sheet current.

19. A method as claimed in claim 18, further comprising the step of displacing the sensor and conductor sheet relative to the structure under inspection, whereby the sheet current can be rotated as the sensor and conductor sheet are guided across the structure without the need for rotating either the sensor or conductor in order to detect anomalies at any point in the structure.

* * * * *